June 21, 1938. C. SALBACH Plant Pat. 280
GLADIOLUS
Filed Sept. 16, 1937
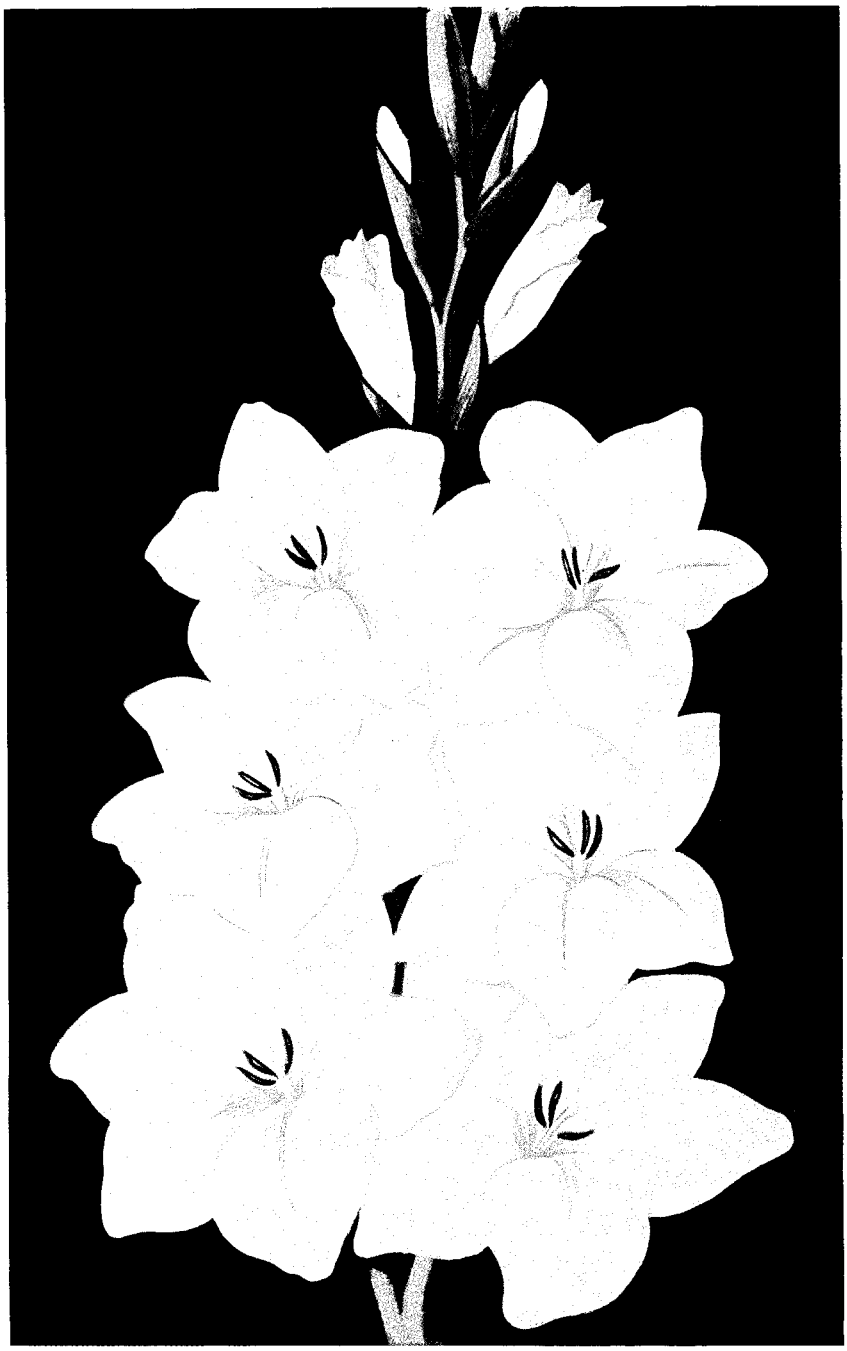
Carl Salbach
INVENTOR
By Orville M. Kile
PLANT PATENT AGENT Patented June 21, 1938

Plant Pat. 280

UNITED STATES PATENT OFFICE

280

GLADIOLUS

Carl Salbach, Contra Costa County, Calif., assignor to Ella S. Salbach, Contra Costa County, Calif.

Application September 16, 1937, Serial No. 164,247

1 Claim. (Cl. 47—60)

My present invention relates to improvements in flowering gladioli of the type notable for size and quality of bloom. The object of this invention is to provide a gladiolus of superior La France to Geranium Pink coloring, with very large individual flowers of good quality and unusually well-placed and well-formed.

My new gladiolus variety originated as a seedling produced from cross pollination work carried on by myself. To the best of my knowledge and belief, the pollen parent of this new variety was the variety "Festival Queen." My record showing the other parent has been lost. This new variety first bloomed August-September, 1933.

The accompanying illustration shows in reduced size a freshly cut spike of my new variety, as true to nature as the artist could paint it. It must be understood, however, that the painting cannot depict the softness of the coloring of the natural flower.

Following is a more complete description of the plant and flower of this new variety.

*The plant*

The plant is a very vigorous grower and the tips of the spikes usually reach a height of 60 to 75 inches above the ground. Foliage is very moderate in quantity and Empire Green (Plate XXXII, Ridgway's Color Standards and Nomenclature) in color. Stems are stiff and strong and fully adequate to hold the heavy flower spike in upright position.

The spikes are much taller than those of somewhat similar varieties of light or Geranium Pink gladioli grown under the same conditions of soil and climate. Usually each spike opens five to seven of its huge flowers at one time, and has a total of seventeen or eighteen flowers in all.

*The spike and flower*

The individual flowers are exceptionally large, the lower blossoms usually being over six inches across and sometimes reaching even seven or eight inches in width.

These flowers consist of six petals of rather uniform size and shape. The petals are smooth and unwrinkled, somewhat heart shaped, and have unnotched and unwrinkled edges. They are of heavy substance, thus making the variety very valuable for shipping and long keeping.

Three white stamens arise from the center of the throat and these are topped with very large anthers which are covered with much pollen and are of Auricula Purple color (Plate XXVI). Arising from the center of the stamens and extending considerably beyond the anthers is a single slender, white style which terminates in three short, spreading branches.

The color in Ridgway's Color Standards and Nomenclature which most nearly approaches the color of this new variety is in general effect between La France Pink and Geranium Pink (Plate I). It is La France Pink in the center, the petals deepening in shade toward their edges, the outer edge being between Geranium Pink and Rose Doree (Plate I). The throat is marked with a faint feathering of Spectrum Red (Plate I).

Other known varieties of somewhat similar coloring have much smaller flowers. Festival Queen, the closest approach to this new variety in similarity, is not so tall, has smaller flowers, and its petal substance is not so firm. All other known varieties of similar color—such as Alma Needham—are much smaller.

The most notable characteristics which readily distinguish my new gladiolus from all other known La France or light pink toned varieties, and particularly from Festival Queen and Alma Needham, are:

1. The very large size and regular formation of the flowers.
2. The heavy substance of the flowers.
3. The vigorous growth and resultant long spikes.
4. The soft, clear smoothness of the coloring.
5. The unusually good keeping and shipping qualities.
6. The general symmetry of placement of flowers.

Having thus disclosed my invention, I claim:

The new variety of gladiolus plant herein described and illustrated, characterized particularly by its vigor of growth and the resulting length of spike, its general symmetry and its flowers of huge size, heavy substance, and soft, clear coloring as described.

CARL SALBACH.